United States Patent [19]

Smyth et al.

[11] 4,393,883
[45] Jul. 19, 1983

[54] SINGLE PASS A-V LEAD

[75] Inventors: Nicholas P. D. Smyth, Bethesda, Md.; Jeanne M. Lesniak, Columbia Heights; Kenneth B. Stokes, Brooklyn Park, both of Minn.

[73] Assignee: Medtronic, Inc., Minneapolis, Minn.

[21] Appl. No.: 203,298

[22] Filed: Nov. 3, 1980

[51] Int. Cl.$^3$ .............................................. A61N 1/04
[52] U.S. Cl. .................................. 128/785; 128/419 P
[58] Field of Search ................... 128/419 P, 784, 785, 128/786

[56] References Cited

U.S. PATENT DOCUMENTS

| | | | |
|---|---|---|---|
| 3,866,615 | 2/1975 | Hewson | 128/419 D |
| 3,976,082 | 8/1976 | Schmitt | 128/785 |
| 4,057,067 | 11/1981 | LaJos | 128/785 |
| 4,289,144 | 9/1981 | Gilman | 128/419 P |
| 4,332,259 | 6/1982 | McCorkle, Jr. | 128/786 |

FOREIGN PATENT DOCUMENTS 2605590 8/1977 Fed. Rep. of Germany ... 128/419 P

OTHER PUBLICATIONS

Lead Manual for the Medtronic 6990U and 6991U Atrial Pacing Leads, MC 79 PE 0342, Aug. 1979, 10 pp.

Primary Examiner—William E. Kamm
Attorney, Agent, or Firm—Reed A. Duthler; John L. Rooney; Joseph F. Breimayer

[57] ABSTRACT

A dual chamber pacing lead requiring but a single transvenous pass for implantation. The ventricular electrode has tines for sustaining acute and chronic fixation. The ventricular electrode is coupled to a first conductor which is space wound having an insulation sheath. The proximal end of the first space wound coil protrudes slideably from a first connector pin of a bifurcated connector assembly. An optional stylet may be inserted into the first space wound coil to assist in ventricular placement. A second space wound coil is slideably located over the first space wound coil. The second space wound coil serves as a support means rather than a conductor. The proximal end of the second space wound coil is fixedly attached to the connector assembly. The first space wound coil protrudes near the distal end of the second space wound coil. A third space wound coil having an insulating sheath serves as a conductor having the distal end attached to the tined atrial electrode and the proximal end coupled to a second pin of the bifurcated cable. The distal end of the third space wound coil is located coaxially within the second space wound coil. A stylet straightens the distal end of the third space wound coil which assumes a "J" shaped upon removal of the stylet. An outer sheath encloses the second and third space wound coils from the bifurcated connector to the atrial electrode.

6 Claims, 6 Drawing Figures

SINGLE PASS A-V LEAD

BACKGROUND OF THE INVENTION

1. Field of the Invention

The present invention generally relates to medical devices and more specifically relates to surgically implantable electrodes.

2. Description of the Prior Art

The earliest cardiac pacers involved electrical stimulation of a single chamber (i.e., right ventricle) of the heart. Indeed, this is still the most prevalent technique. However, a number of medical conditions are more effectively treated using stimulation to two chambers (i.e., right atrium and right ventricle) or using a combination of sensing in one chamber and stimulation in another.

The desired dual chamber pacing (i.e., by an electrode in each of the right atrium and the right ventricle) is most commonly accomplished using two separate leads. This is relatively convenient for epicardial applications, but may be a problem for transvenous insertion of electrodes. Some techniques are two veins whereas others involve insertion of two leads in a single vein. However, a single pass dual chamber lead is in demand.

An early single pass A-V (atrial and ventricular) lead was taught by Bures in U.S. Pat. No. 3,865,118. Because the configuration taught by Bures requires the ventricular lead to be coaxially mounted within the outer sheath, minimal control can be exercised over placement of the atrial electrodes. To compensate for this lack of control, Bures teaches the use of opposing (i.e., spaced by 180°) spring loaded electrodes. Such a placement technique has been shown to be susceptible to dislodgement and is electrically inefficient because of the relatively large surface area of the electrode and the difficulty in controlling the amount of that surface area actually in contact with the atrial wall. Furthermore, using the outer catheter to control flexure of the atrial electrodes has lead to sealing problems. The alternative embodiment of FIG. 5 overcomes a number of these problems by attaching the atrial electrodes directly to the outer catheter. Unfortunately this configuration is electrically very inefficient because contact between the atrial electrodes and the endocardium cannot be assured chronically.

Lajos in U.S. Pat. No. 4,057,067 solves many of the control problems found with the lead taught by Bures by using a "J" shaped atrial lead with stylet control. However, because the atrial and ventricular leads are spaced at a fixed distance, the lead taught by Lajos does not accommodate hearts having varying distances between the right ventricular apex and the right atrial appendage which are the most desired sites for location of the electrodes. A further problem with the Lajos lead is the establishment of an effective seal of the hole at the distal end of the atrial electrode. During insertion, this hole is blocked by the stylet. However, removal of the stylet causes seepage of blood into the lead.

A third single pass lead configuration is taught by Sabel in U.S. Pat. No. 3,949,757. Sabel uses the "J" shaped atrial electrode placement as taught by Lajos but slides the atrial catheter within the outer sheath of the ventricular catheter. This tends to solve one problem of Lajos but not requiring an aperture in the distal end of the atrial electrode for stylet straightening of the "J" shape. It does not completely solve the problem of differing heart sizes, however. The distance between the distal end of the atrial catheter and the distal end of the outer sheath 28 is essentially fixed by practical factors even though the atrial catheter is slideably mounted within outer sheath 28, because sliding of the atrial catheter also changes the shape of the "J". This may be viewed in FIG. 7. The atrial electrode may be lowered in the atrium by moving the atrial catheter either proximal or distal relative to the outer sheath. However, the atrial electrode may not be raised within the atrium. That distance is effectively established by the prior implantation of the ventricular electrode. Providing a larger distance between the ventricular electrode and the distal end of outer sheath 28 would tend to distort the "J" shape of the atrial catheter.

SUMMARY OF THE INVENTION

The present invention provides a single pass lead which overcomes the problems identified in the prior art structures. Maximum control is assured by providing what is essentially an atrial lead having a "J" shape and stylet control with a slideably mounted ventricular lead. The ventricular lead has optional stylet control. The structure permits positioning of the atrial electrode first. This is important as this may be the most difficult step particularly for atrial sensing. Placement of the ventricular electrode then proceeds in the normal manner. Tines or other positive fixation devices are provided for both ventricular and atrial electrodes to establish acute and chronic stability. The atrial and ventricular leads are each independently sealed with an insulating sheath. An outer space wound coil is used to provide overall mechanical support. The outer sheath is also sealed. A bifurcated connector is provided for coupling to a pulse generator.

DETAILED DESCRIPTION OF THE PREFERRED EMBODIMENTS

The present invention is described in its preferred embodiment having unipolar ventricular and atrial electrodes. However, configurations employing bipolar electrodes and other similar variations will be seen to be within the intended scope of the following discussion.

CONSTRUCTION

Figure 1:
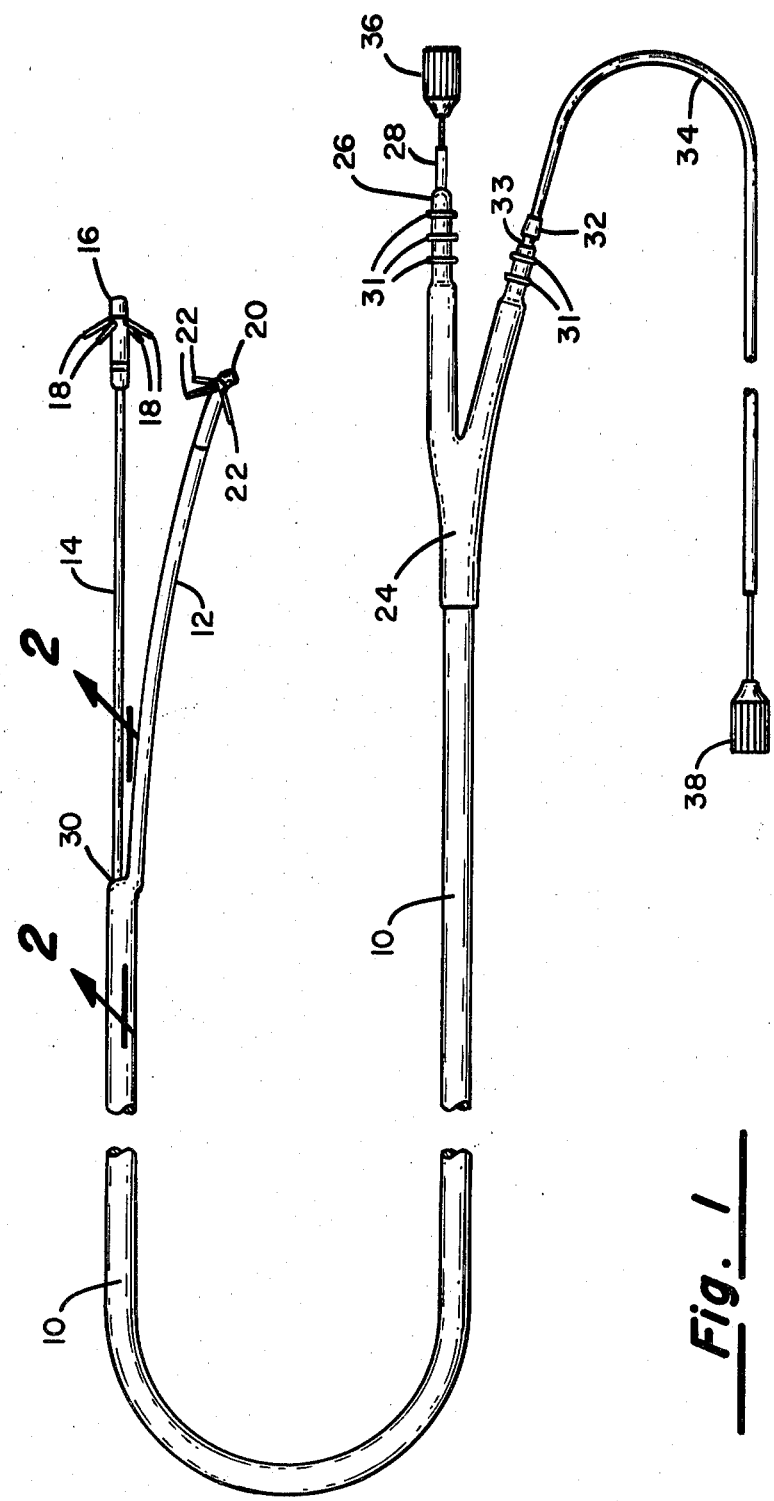
FIG. 1 is a plan view of a single pass lead incorporating the present invention.

FIG. 1 is a plan view of a lead incorporating the present invention. Ventricular electrode 16 is located at the distal end of ventricular lead 14. Tines 18 serve to positively affix ventricular electrode 16. Atrial electrode 20 is located at the distal end of atrial lead 12. Atrial electrode 20 is positioned at an angle relative to the axis of atrial lead 12 to ensure chronic stability. A further description of this technique may be found in U.S. Pat. No. 3,939,843 issued to Smyth.

Atrial lead 12 has a "memory coil" which assumes a "J" shape upon removal of stylet 36. As is discussed below, atrial lead 12 is an extension of the main body of the lead. Similarly, outer sheath 10, which covers the main body of the lead extends from junction 30 to cover atrial lead 12 up to atrial electrode 20. The details of junction 30 are discussed below. Tines 22 provide stability for atrial electrode 20.

Bifurcated connector 24 is used to electrically couple the atrial and ventricular electrodes to a pulse generator (not shown). Connector pin 28 is coupled via a space wound coil of wire to atrial electrode 20. Insulation 26 provides a seal between the pulse generator and bifurcated connector 24 using sealing rings 31. Stylet 36 is inserted into an aperture in connector pin 28 and proceeds through the space wound coil of wire to the distal end of atrial lead 12 near atrial electrode 20.

Ventricular electrode 16 is coupled to another space wound conductor coil which passes through ventricular lead 14, outer sheath 10, bifurcated connector 24, insulator 32 and emerges as proximal length 34 of the ventricular lead. Since the ventricular lead is slideable, proximal length 34 is cut to proper length after electrode placement is described below and a connector pin (not shown) is added. Optional stylet 38 is inserted into proximal length 34 and proceeds to near ventricular electrode 16. Two sealing rings 31 are molded into insulator 32. After proximal length 34 is cut and the connector pin added, an "0" ring (not shown) is inserted into groove 33 providing the third sealing ring. Preparing the proximal end of the sliding ventricular lead is discussed in greater detail in U.S. Pat. No. 4,289,144 entitled "A-V Sidearm Lead," assigned to the assignee of the present invention.

Figure 2:
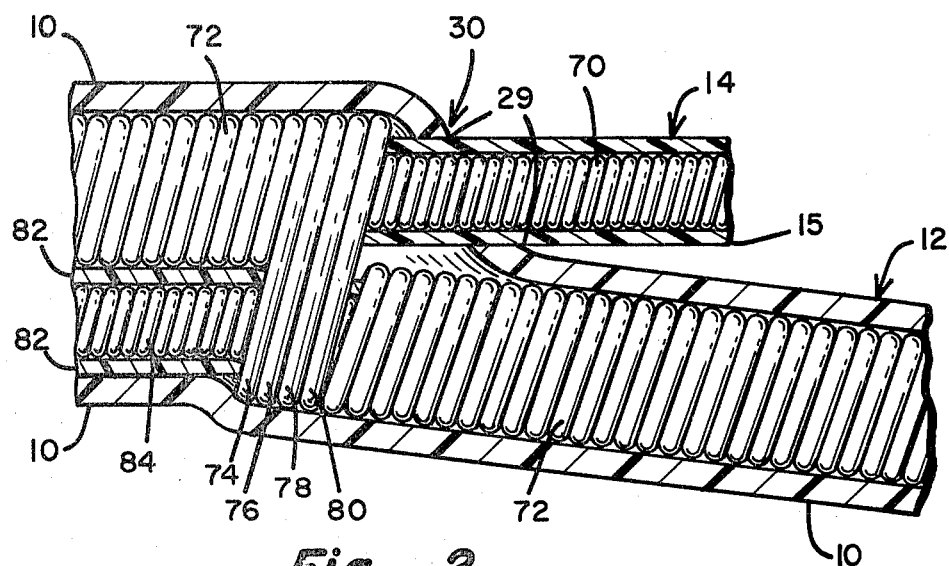
FIG. 2 shows the construction of the junction.

FIG. 2 shows a detailed view of junction 30 with outer sheath 10 partially cut away. Ventricular lead is seen as comprising insulating sheath 15 and space wound conductor coil 70. As stated above, the distal end of coil 70 is coupled to ventricular electrode 16. Proximal length 34 of ventricular lead 14 extends from bifurcated connector (see also FIG. 1). Space wound coil 72 is a quadrafilar coil which is not used as an electrical conductor but merely supplies mechanical stability. Coil 72 is constructed of separate wires 74, 76, 78 and 80 as shown. Coil 72 is wound around ventricular lead 14 proximal to junction 30. Distal to junction 30, ventricular lead 14 emerges from coil 72 as shown. The "J" shape is established by coil 72 using known techniques.

Atrial lead 12 is shown as containing space wound conductor coil 84 which electrically couples connector pin 28 to atrial electrode 20 (see also FIG. 1). Coil 84 is insulated along its length by sheath 82. Distal to junction 30, coil 72 is wound about coil 84 and sheath 82. Outer sheath 10 encloses coil 72 along its entire length. Coil 84 and sheath 82 are also enclosed by outer sheath 10 as shown. Ventricular lead 14 exits coil 72 and outer sheath 10 at junction 30. To provide the desired control, ventricular lead 14 must slide relative to aperture 29 of outer sheath 10 at junction 30. To provide the desired control, ventricular lead 14 must slide relative to aperture 29 of outer sheath 10. Aperture 29 is sealed using silicone grease to prevent ingress of body fluids.

Figure 3:
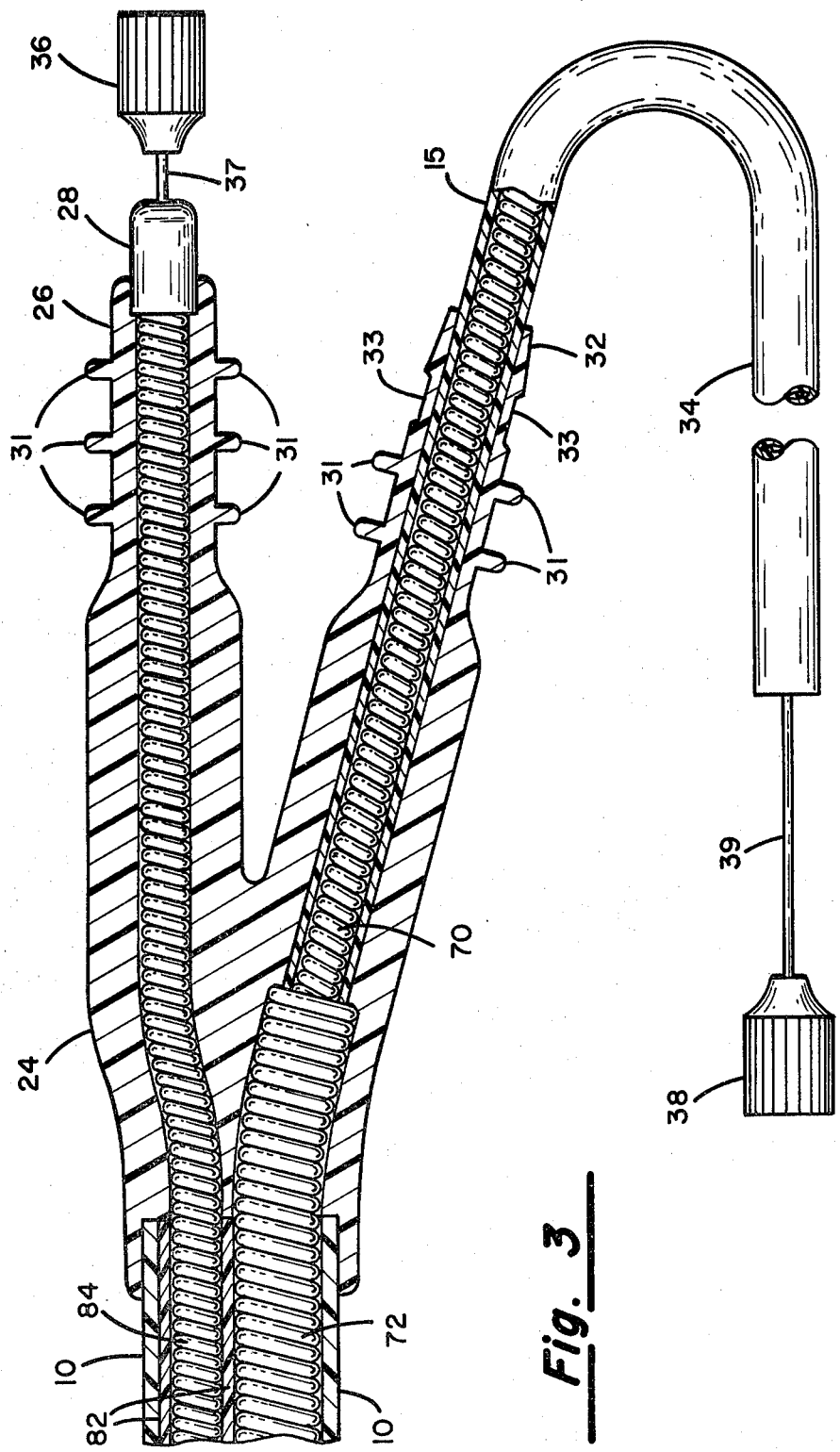
FIG. 3 shows the bifurcated connector.

FIG. 3 shows a detailed view of bifurcated connector 24 with insulation partially cut away. Outer sheath 10 is sealably attached to bifurcated connector 24. Coil 84 is electrically controlled to connector pin 28 by any suitable technique. Sheath 82 is sealably attached to bifurcated connector 24. Stylet 36 is seen as having stylet wire 37 inserted into an aperture (not shown) in connector pin 28. Stylet wire 37 extends to near atrial electrode 20 within coil 84. Coil 72 is attached to bifurcated connector 24. Coil 70, insulated by sheath 15, slideably protrudes from the proximal end of coil 72 and bifurcated connector 24 as shown. This protrusion is proximal length 34 having stylet wire 39 inserted therein. As explained above, proximal length 34 is cut after ventricular electrode 16 is positioned. A connector pin is inserted into insulator 32 to provide electrical coupling to a pulse generator. An "0" ring is positioned over groove 33 to complete the seal

OPERATION

Figure 4:
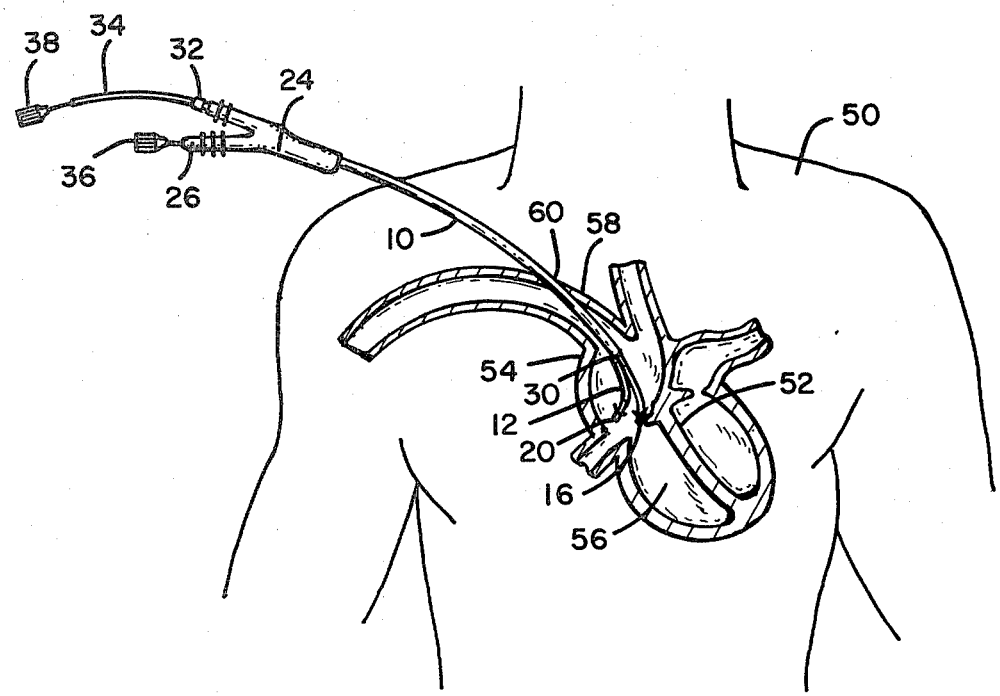
FIG. 4 shows transvenous insertion of the single pass lead into the right atrium.
Figure 5:
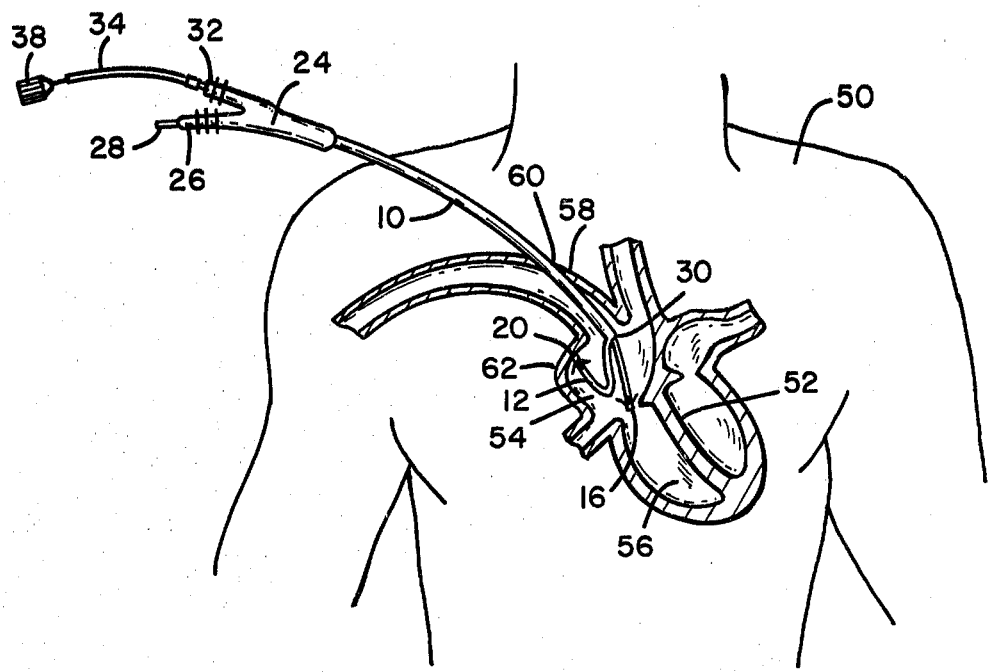
FIG. 5 shows removal of the atrial stylet.
Figure 6:
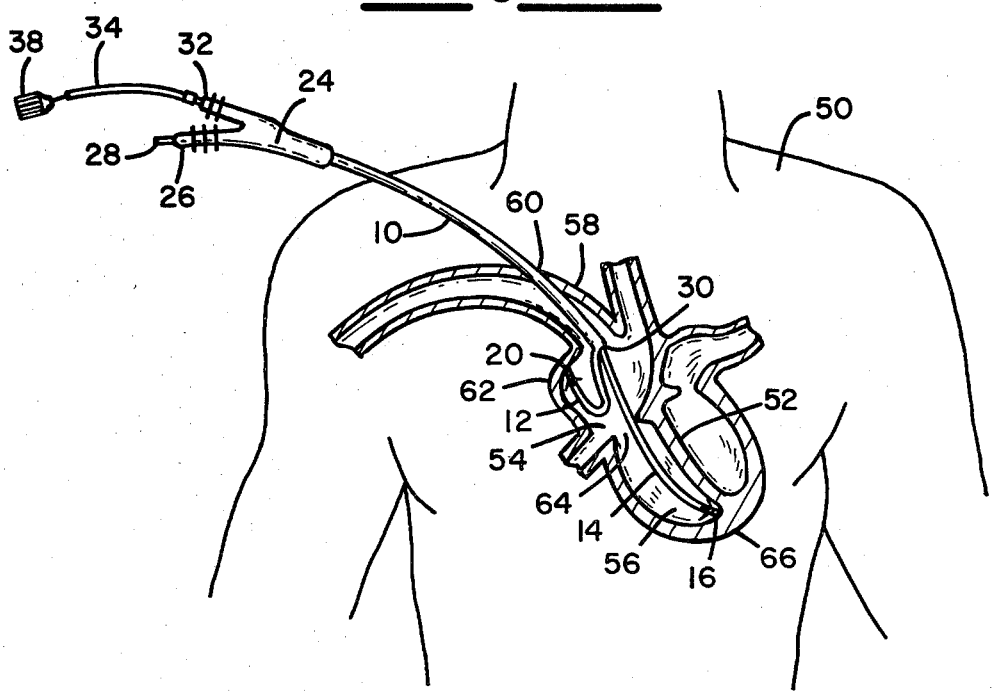
FIG. 6 shows placement of the ventricular electrode.

FIGS. 4, 5 and 6 depict the basic implantation technique currently envisioned. FIG. 4 shows the single pass lead during initial insertion. In preparation, proximal length 34 is pulled until ventricular electrode 16 is located at junction 30. This makes the single pass lead perform as if a single electrode (i.e., atrial electrode 20) were at the distal tip. Stylet 36 is required. Stylet 38 is shown inserted but is optional.

Atrial electrode 20 is inserted into vein 58 through incision 60 using normal procedures. Atrial electrode 20 is guided into right atrium 54 of heart 52 to produce the situation shown in FIG. 4.

Removal of stylet 36 causes the memory coil of atrial lead 12 to assume the "J" shape as shown. The memory coil is actually the distal portion of coil 72 (see also FIG. 2). Care is exercised to properly position atrial electrode 20 into the desired area 62 of right atrium 54. Threshold measurements are taken, and atrial electrode 20 is repositioned as required.

After satisfactorily securing atrial electrode 20 ventricular lead 14 is advanced through tricuspid valve 64 by distal force on proximal length 34. In the normal fashion, ventricular electrode 16 is secured at ventricular apex 66 of right ventricle 56. Threshold measurements are taken, and ventricular electrode 16 is repositioned as required. After both electrodes (i.e., atrial electrode 20 and ventricular electrode 16) are satisfactorily positioned, optional stylet 38 is removed. Outer sheath 10 is anchored at incision 60 and the incision is closed.

Proximal length 34 is cut to proper length. An "0" ring is positioned on insulator 32 (see also FIGS. 1 and 3). A connector pin (not shown) is inserted and bifurcated connector 24 is coupled to a pulse generator (not shown). For additional discussion of cutting proximal length 34 and subsequent steps please consult the teachings of Gilman in the above-identified reference.

What is claimed is:

1. A single pass dual chamber pacing lead comprising:
   a connector;
   an outer sheath having a proximal end attached to said connector and having a distal end and having a junction point intermediate said proximal end and said distal end, said outer sheath having a "J" shaped bend located intermediate said distal end and said junction point;
   a first space wound coil conductor located within said outer sheath having a proximal end coupled to said connector and having a distal end;
   an atrial electrode coupled to said distal end of said first space wound coil conductor;
   a first stylet removeably insertable in said first space wound coil conductor which when inserted substantially straightens said outer sheath and whereby placement of said atrial electrode is controlled;
   a ventricular electrode;

a second space wound coil conductor slideably located within said outer sheath between said proximal end and said junction point of said outer sheath having a distal end attached to said ventricular electrode, said first and second space wound coil conductors mutually insulated, said second space wound coil conductor slideable in a proximal direction within said outer sheath whereby said second space wound coil conductor may be substantially withdrawn into said outer sheath;

a second stylet insertable in said second space wound coil conductor whereby placement of said ventricular electrode is controlled; and a space wound coil located within said outer sheath and having a proximal end attached to said connector and a distal end attached to said atrial electrode located coaxially about said first conductor between said junction point and said atrial electrode and located coaxially about said second conductor between said junction point and said connector.

2. A single pass dual chamber pacing lead according to claim 1 further comprising:

first means for chronically affixing said ventricular electrode to body tissue.

3. A single pass dual chamber pacing lead according to claim 2 further comprising second means for chronically affixing said atrial electrode to body tissue.

4. A single pass dual chamber pacing lead comprising:

a first sheath having a proximal end, a distal end, a lumen, and an aperture open to the lumen of said first sheath located intermediate the proximal end of said first sheath and the distal end of said first sheath;

a first conductor coil having a proximal end and a distal end, mounted within said first sheath;

a second sheath having a proximal end and a distal end, slideably mounted within the lumen of said first sheath and exiting said first sheath through the aperture in said first sheath;

a second conductor coil having a proximal end and a distal end, mounted within said second sheath;

a first electrode electrically coupled to the distal end of said first conductor coil;

a second electrode electrically coupled to the distal end of said second conductor coil;

a structural coil surrounding said second sheath intermediate the proximal end of said first sheath and the aperture of said first sheath and surrounding said first conductor intermediate the distal end of said first sheath and the aperture of said first sheath, said structural coil imparting a bend to said first sheath intermediate the aperture of said first sheath and the distal end of said first sheath;

a first stylet removeably insertable in said first conductor coil whereby placement of said first electrode is controlled and which when inserted substantially straightens said first sheath; and a second stylet removeably insertable in said second conductor coil whereby placement of said second electrode is controlled.

5. A dual chamber pacing lead according to claim 4 wherein said structural coil imparts a "J" shaped bend to the first sheath intermediate the aperture of said first sheath and the distal end of said first sheath.

6. A single pass dual chamber lead according to claim 5 wherein said second sheath is slideable proximally within said first sheath whereby said second sheath may be substantially withdrawn into said first sheath.

* * * * *

UNITED STATES PATENT AND TRADEMARK OFFICE
CERTIFICATE OF CORRECTION

PATENT NO. : 4,393,883

DATED : July 19, 1983

INVENTOR(S) : SMYTH et al

It is certified that error appears in the above-identified patent and that said Letters Patent are hereby corrected as shown below:

Abstract,
    4th line from bottom, ""J" shaped" should be --"J" shape--;

Column 1,
    line 23, "are" should be --use--;

Column 2,
    line 22, after "ventricular lead" insert --also--;
    line 22, delete "optional";

Column 3,
    line 20, "is" should be --as--;

line 63, "controlled" should be --coupled--.

Signed and Sealed this

Sixth Day of December 1983

[SEAL]

Attest:

GERALD J. MOSSINGHOFF

*Attesting Officer*     *Commissioner of Patents and Trademarks*